US00PP37256P2

(12) United States Plant Patent
Mathey

(10) Patent No.: US PP37,256 P2
(45) Date of Patent: Feb. 10, 2026

(54) ***HYDRANGEA* PLANT NAMED 'SMNHPLK'**

(50) Latin Name: *Hydrangea paniculata*
Varietal Denomination: SMNHPLK

(71) Applicant: Megan M. Mathey, Holland, MI (US)

(72) Inventor: Megan M. Mathey, Holland, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/964,969

(22) Filed: Dec. 2, 2024

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

(56) References Cited

PUBLICATIONS

Proven Winners Powerball Panicle *hydrangea*, retrieved on Jun. 11, 2025 at https://www.provenwinners.com/plants/hydrangea/powerball-panicle-hydrangea-hydrangea-paniculata, 5 pp. (Year: 2025).*
T&T Seeds 2025 Catalogue, retrieved on Jun. 11, 2025 at https://ttseeds.com/wp-content/uploads/2024/12/TT_2025-Catalogue_WEB.pdf?srsltid=Afm BOoo5f0myilFKg2k5E-tdrN4A-8sXUwVziX0Sy-dmpaGywE7BteUS, pp. 1-4, 83, 96-98. (Year: 2025).*

* cited by examiner

*Primary Examiner* — June Hwu

(57) ABSTRACT

A new and distinct cultivar of *Hydrangea* plant named 'SMNHPLK' is disclosed, characterized by exceptionally dense mophead panicles with a distinct spherical shape. Sepals open light emerald green, then mature to white and red-pink and aging to entirely red-pink. Stems are strong and thick, supporting large flower panicles without flopping. Plants are compact and upright with heavy flower coverage. The new variety is a *Hydrangea*, typically produced as an outdoor ornamental plant.

4 Drawing Sheets

Latin name of the genus and species: *Hydrangea paniculata.*

Variety denomination: 'SMNHPLK'.

BACKGROUND OF THE INVENTION

The new cultivar is a product of a planned breeding program conducted by the inventor to produce new *Hydrangea paniculata* cultivars with strong stems, large panicles, compact habits, and attractive flower aging. The crossing resulting in the new cultivar was made in summer of 2018 at a nursery in Grand Haven, Michigan.

The seed parent is the cultivar *Hydrangea paniculata* 'Limelight' U.S. Plant Pat. No. 12,874. The pollen parent is an unpatented internal selection of *Hydrangea paniculata* named 'Stratus'. The new cultivar was found and selected by the inventor in summer of 2019 at the same nursery in Grand Haven, Michigan. Asexual reproduction of the new cultivar 'SMNHPLK' was first performed during summer of 2019 in Grand Haven, Michigan, by softwood cuttings. Through subsequent propagation, multiple additional generations have been reproduced, having shown that the unique features of this cultivar are stable and reproduced true to type.

SUMMARY OF THE INVENTION

The cultivar 'SMNHPLK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHPLK'. These characteristics in combination distinguish 'SMNHPLK' as a new and distinct *Hydrangea* cultivar:

1. Exceptionally dense mophead flower panicles.
2. Flower panicles which are distinctly spherical.
3. Flower sepals which open light emerald green before maturing to white and red-pink, then aging entirely red-pink.
4. Compact, upright habit.
5. Strong stems which support the large flower panicles without "flopping."
6. Heavy flower coverage.
7. Healthy, dark green foliage.

PARENT COMPARISONS

Plants of 'SMNHPLK' are similar to plants of the seed parent in most horticultural characteristics, however, plants of 'SMNHPLK' differ in the following:

1. Plants of the new cultivar are smaller at maturity than plants of the seed parent.
2. Branching habit of the new cultivar is tighter than the branching habit of the seed parent.
3. Flower panicles of the new cultivar are more dense than flower panicles of the seed parent.

Plants of 'SMNHPLK' are similar to plants of the pollen parent in most horticultural characteristics, however, plants of 'SMNHPLK' differ in the following:

1. Flower panicles of the new cultivar are mophead, while flower panicles of the pollen parent are lacecap.
2. Flower panicles of the new cultivar are more dense than flower panicles of the pollen parent.

COMMERCIAL COMPARISON

Plants of 'SMNHPLK' can be compared to plants of the commercial cultivar *Hydrangea paniculata* 'Jane', U.S. Plant Pat. No. 22,330. Plants of 'SMNHPLK' are similar to plants of 'Jane' in most horticultural characteristics, however, plants of 'SMNHPLK' differ in the following:

1. Flower panicles of the new cultivar are more spherical in shape, while flower panicles of this comparator are more conical.
2. Stems of the new cultivar are stronger than stems of this comparator.
3. Branching habit of the new cultivar is tighter than the branching habit of this comparator.

BRIEF DESCRIPTION OF THE PHOTOGRAPHS

The accompanying photograph in FIG. 1 illustrates in full color a typical plant of 'SMNHPLK' grown in a field in Grand Haven, Michigan. This plant is approximately 3 years old.

Figure 1:
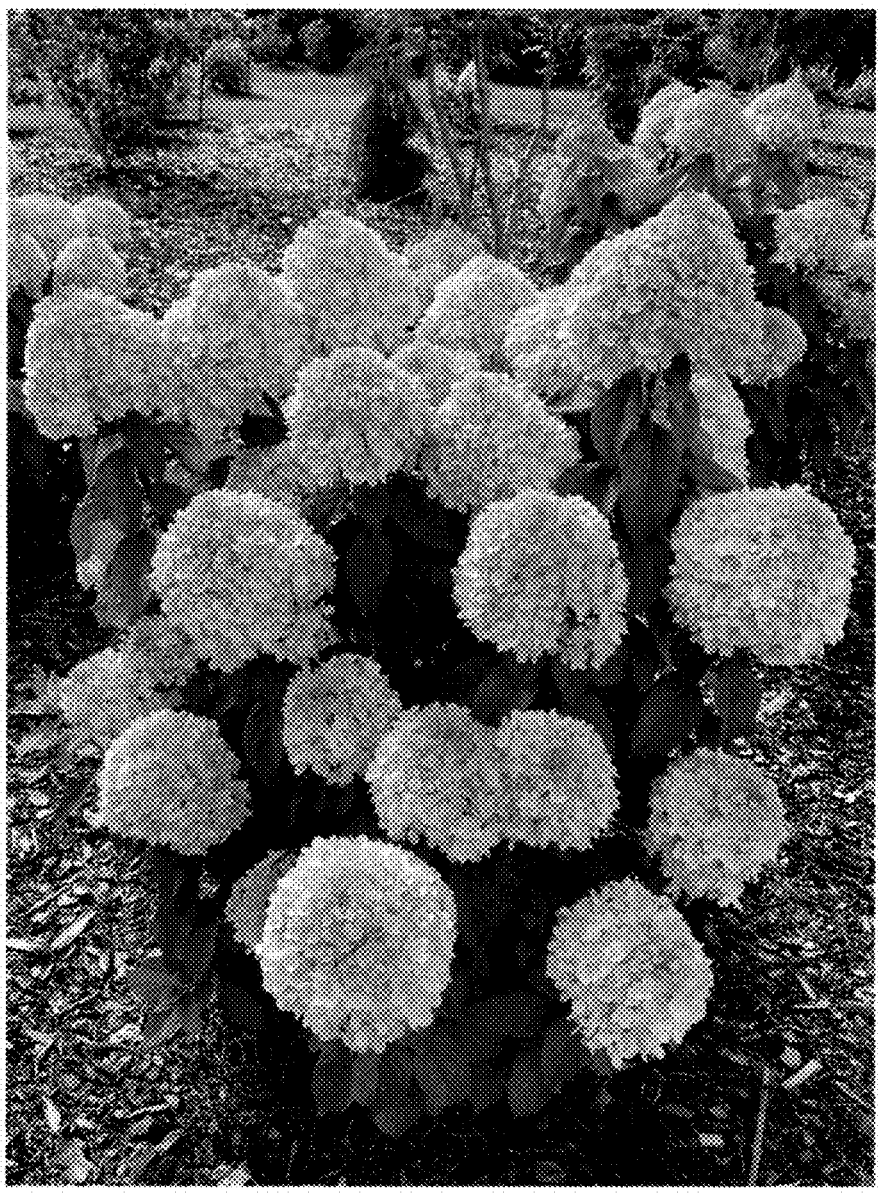
Figure 2:
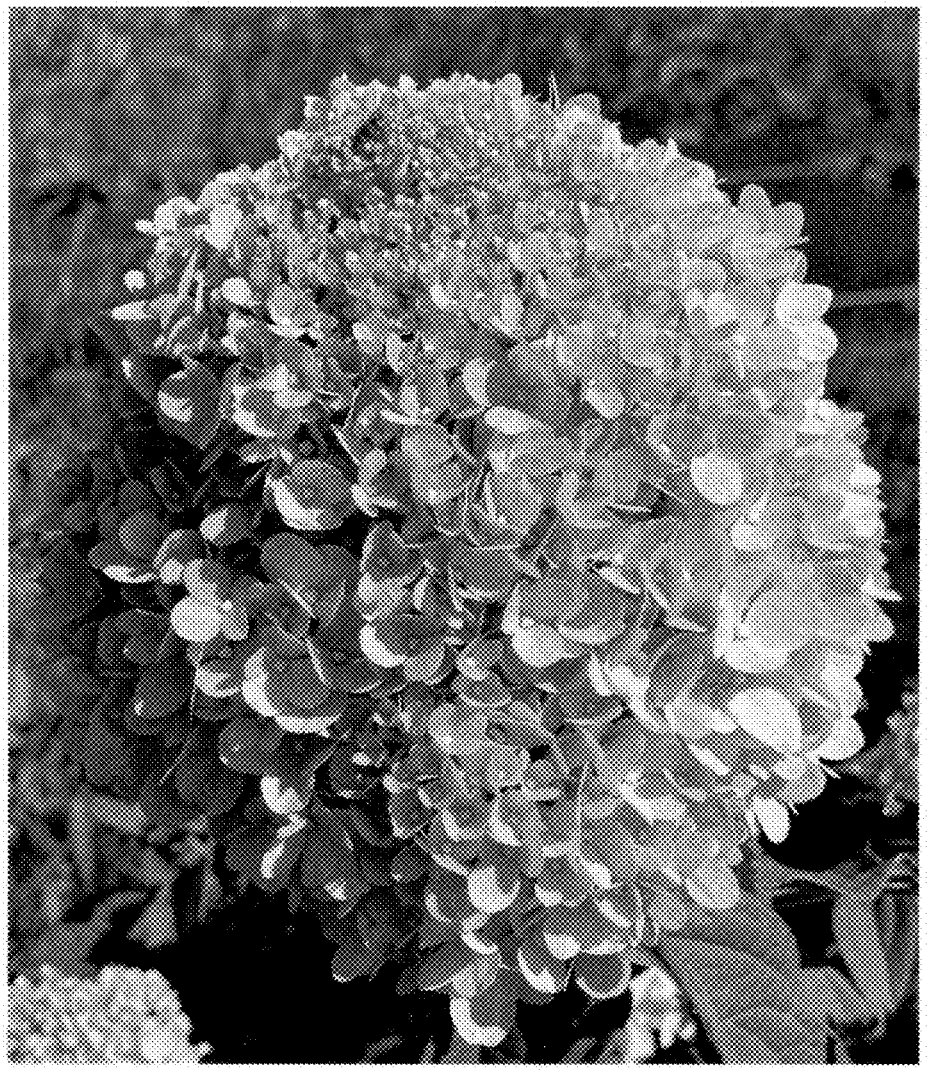
FIG. 2 illustrates in full color a close-up of a developing inflorescence of 'SMNHPLK'.
Figure 3:
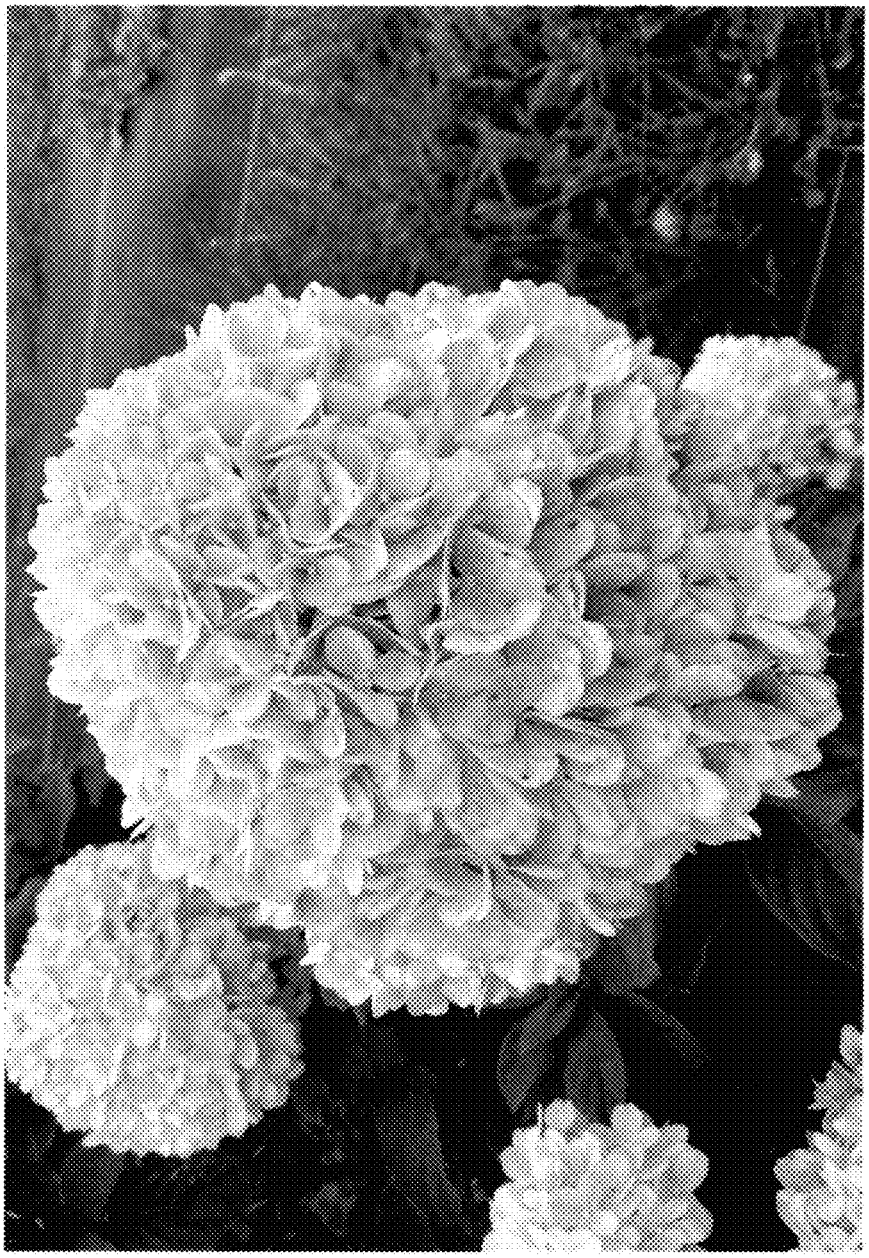
FIG. 3 illustrates in full color a close-up of a mature inflorescence of 'SMNHPLK'.
Figure 4:
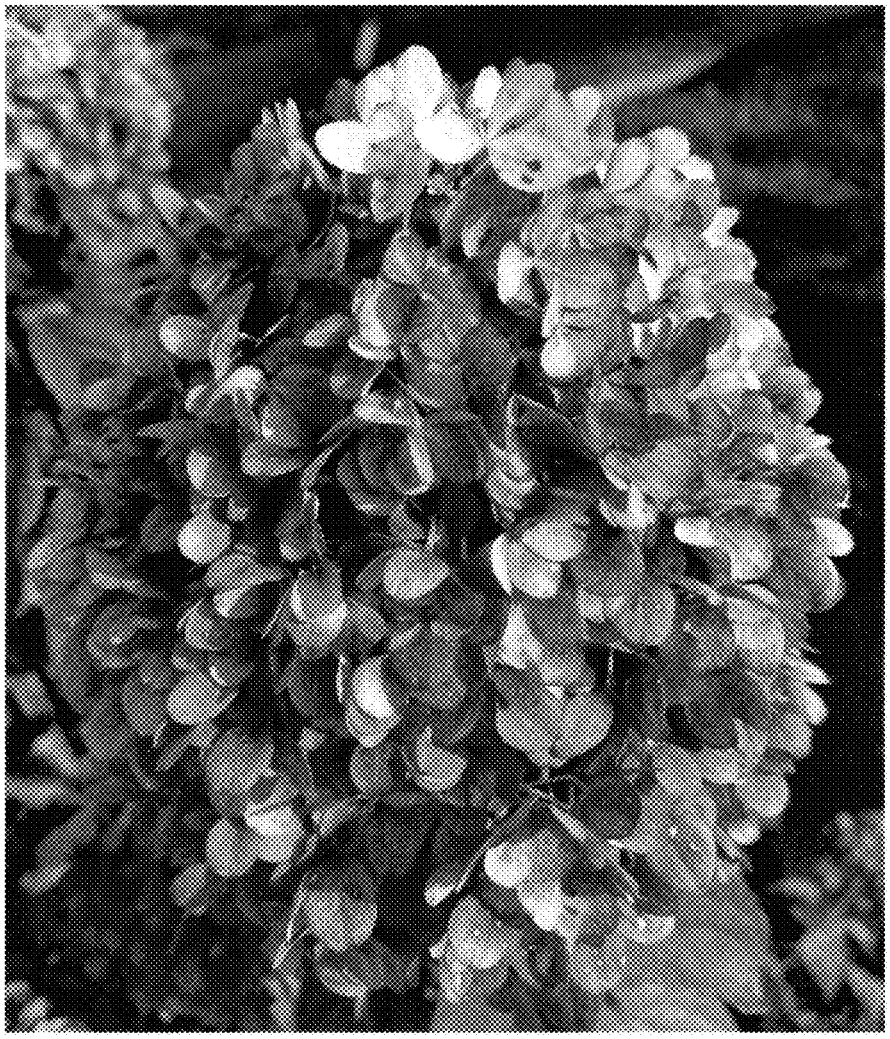
FIG. 4 illustrates in full color a close-up of a fading inflorescence of 'SMNHPLK'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'SMNHPLK' plants grown in a poly-greenhouse in Grand Haven, Michigan. The plants were 2 to 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Hydrangea paniculata* 'SMNHPLK'.

PROPAGATION

Typical method: Softwood cuttings.
Root initiation: 18 days in summer.
Time to produce rooted cutting: 60 days in summer.
Roots: Thin, freely branching, fibrous, moderately dense. Beige in color, not accurately measured with R.H.S. Chart.

PLANT

Growth habit: Upwards and outwards.
Shape: Compact, rounded.
Height: 75 cm.
Plant spread: 80 cm.
Pot size of plant described: #3.
Age of plant described: Approximately 2 to 3 years.
Growth rate: Moderate to fast.
Plant vigor: Moderate to high vigor.
Stem:
- *Branching*.—Basal, some pinching required to encourage a rounded, well-branched habit.
- *Number of lateral branches*.—About 20.
- *Shape*.—Rounded, smooth (non-exfoliating).
- *Color*.—Immature: RHS Yellow-Green 144B. Mature: RHS Grey-Brown N199A with Grey-Brown 199C lenticels.
- *Length*.—60 cm.
- *Width*.—5 mm.
- *Aspect*.—60° to 80°.
- *Strength*.—Strong and rigid; capable of supporting dense flower heads without falling.
- *Pubescence*.—Slight, on new growth only.
- *Stem lenticels*.—Color: Grey-Brown 199C Shape: Oblong Size: Width 0.25 mm. Length 0.5 mm Density: Moderate
- *Internode Length*.—5 cm.

FOLIAGE

Leaf:
- *Arrangement*.—Opposite.
- *Shape*.—Elliptic.
- *Length*.—7.5 cm.
- *Width*.—4.75 cm.
- *Apex*.—Acuminate.
- *Base*.—Rounded, obtuse.
- *Margin*.—Serrate.
- *Texture of top surface*.—Coriaceous, with a light smattering of short, coarse hairs.
- *Texture of bottom surface*.—Coriaceous with raised venation.
- *Pubescence*.—Very slight on upper surface, particularly with young leaves.
- *Leaf anthocyanin*.—Weakly present at petiole.
- *Color*.—Young Foliage, Upper Side: RHS Green 137B. Young Foliage, Under Side: RHS Yellow-Green 147C. Mature Foliage, Upper Side: RHS Green 137B. Mature Foliage, Under Side: RHS Yellow-Green 147C.

Venation:
- *Type*.—Pinnate.
- *Color*.—Mature, Upper Side: RHS Yellow-Green 147C. Mature, Under Side: RHS Yellow-Green 147C.

Petiole:
- *Length*.—1.5 cm.
- *Width*.—2 mm.
- *Color*.—Upper Side: RHS Yellow-Green 147C. Under Side: RHS Yellow-Green 147C.
- *Texture*.—Upper Side: Glabrous. Under Side: Glabrous.

INFLORESCENCE

Natural flowering season: July to September.
Inflorescence type: Mophead.
Panicle:
- *Shape*.—Spherical.
- *Height*.—9 cm.

*Diameter.*—12 cm.
*Longevity.*—Approximately 4 weeks.
Fragrance: None.
Sterile flowers:
*Flowers per inflorescence.*—300 to 400.
*Aspect.*—Upright and outward.
*Shape.*—Whorl.
*Length.*—2 cm.
*Diameter.*—2 cm.
*Depth.*—3 mm.
*Persistence.*—Persistent.
*Longevity.*—Approximately 4 weeks.
Bud:
*Length.*—1.5 mm.
*Diameter.*—1.5 mm.
*Shape.*—Obovate.
*Color.*—RHS Yellow-Green 145C.
Petals:
*Number.*—4.
*Arrangement.*—Cruciform.
*Shape.*—Narrowly elliptic.
*Tip.*—Acute.
*Base.*—Blunt.
*Margin.*—Entire.
*Length.*—2 mm.
*Width.*—1 mm.
*Texture.*—Upper side: Glabrous. Under side: Glabrous.
*Color.*—When Opening, Upper Side: RHS White NN155B. When Opening, Under Side: RHS White NN155B. Fully Opened, Upper Side: RHS White NN155B. Fully Opened, Under Side: RHS White NN155B.
Sepals:
*Number.*—4.
*Arrangement.*—Cruciform. Medium overlap.
*Shape.*—Elliptic.
*Tip.*—Rounded.
*Base.*—Rounded.
*Margin.*—Entire.
*Length.*—1 cm.
*Width.*—6 mm.
*Texture.*—Upper side: Glabrous. Under side: Glabrous.
*Color.*—When Opening, Upper Side: RHS Yellow-Green 145C. When Opening, Under Side: RHS Yellow-Green 145C. Fully Opened, Upper Side: RHS Yellow-Green 145D mixed with White 155A. Flushed Red-Purple 59D. Fully Opened, Under Side: Between RHS Yellow-Green 145D mixed with White 155A. Flushed Red-Purple 59D. Fading, upper side: RHS Red-Purple 59D. Fading, under side: RHS Red-Purple 59D.
Pedicel:
*Length.*—1 cm.
*Diameter.*—1 mm.
*Angle.*—45° to 90°.
*Strength.*—Good, somewhat flexible.
*Texture.*—Slightly pubescent.
*Color.*—RHS Yellow-Green 145D.
Fertile flowers:
*Flowers per inflorescence.*—300 to 400.
*Aspect.*—Upright and outward.
*Shape.*—Whorl.
*Length.*—6 mm.
*Diameter.*—6 mm.
*Depth.*—4 mm.
*Persistence.*—Self-cleaning.
*Longevity.*—1 week on plant.
Bud:
*Length.*—3 mm.
*Diameter.*—3 mm.
*Bud shape.*—Obovate.
*Bud color.*—RHS Yellow-Green 145C.
Petals:
*Number per flower.*—5.
*Arrangement.*—Stellate.
*Shape.*—Narrowly elliptic.
*Tip.*—Acute.
*Base.*—Blunt.
*Margin.*—Entire.
*Length.*—3 mm.
*Width.*—1 mm.
*Texture.*—Upper Side: Glabrous. Under Side: Glabrous.
*Color.*—When Opening, Upper Side: RHS White NN155B. When Opening, Under Side: RHS White NN155B. Fully Opened, Upper Side: RHS White NN155B. Fully Opened, Under Side: RHS White NN155B.
Sepals: Sepals are inconspicuous.
Pedicel:
*Length.*—1 mm.
*Diameter.*—1 mm.
*Angle.*—45°.
*Strength.*—Good.
*Texture.*—Glabrous.
*Color.*—RHS Yellow-Green 144C.

REPRODUCTIVE ORGANS

Sterile flower:
Stamens:
*Number.*—8.
*Filament length.*—2 mm.
*Filament color.*—RHS White N155B.
Anthers:
*Shape.*—Globose.
*Length.*—0.5 mm.
*Color.*—RHS Greyed-Yellow 162D.
*Pollen amount.*—Sparse.
*Pollen color.*—RHS Greyed-Yellow 162D.
Pistil:
*Number.*—1.
*Length.*—1 mm.
Stigma:
*Shape.*—Peltate.
*Color.*—RHS Yellow-Green 144C.
*Style length.*—1 mm.
*Style color.*—RHS Yellow-Green 144C.
*Ovary color.*—RHS Yellow-Green 144A.
Fertile flower:
Stamens:
*Number.*—10.
*Filament length.*—4 mm.
*Filament color.*—RHS White N155B.
Anthers:
*Shape.*—Globose.
*Length.*—0.5 mm.
*Color.*—RHS Greyed-Yellow 162D.
*Pollen amount.*—Sparse.
*Pollen color.*—RHS Greyed-Yellow 162D.

Pistil:

*Number.*—1.

*Length.*—2 mm.

Stigma:

*Shape.*—Peltate.

*Color.*—RHS Yellow-Green 144C.

*Style length.*—1 mm.

*Style color.*—RHS Yellow-Green 144C.

*Ovary color.*—RHS Yellow-Green 144A.

SEEDS

Quantity: Each flower produces a capsule which gives rise to tens of minute seeds. Seeds are very fine and dust-like.

Shape: Narrowly-elliptic or sickle-shaped.

Length: Less than 1 mm.

Diameter: Less than 1 mm.

Color: RHS Grey-Brown N199B.

OTHER CHARACTERISTICS

Disease and pest resistance: Neither resistance nor susceptibility to the normal diseases and pests of *Hydrangea* has been observed.

Drought tolerance and cold tolerance: Hardy to USDA Zones 3-8.

What is claimed is:

1. A new and distinct cultivar of *Hydrangea* plant named 'SMNHPLK' as herein illustrated and described.

* * * * *